(12) United States Patent
MacIsaac et al.

(10) Patent No.: US 7,807,446 B2
(45) Date of Patent: Oct. 5, 2010

(54) HIGH THROUGHPUT SYSTEM AND METHODS FOR ANALYZING LIQUID FORMULATIONS

(75) Inventors: Susan MacIsaac, Chesterfield, MO (US); Timothy Ottens, Stanton, MO (US); Kevin Deppermann, St. Charles, MO (US); Angela Koestel, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 849 days.

(21) Appl. No.: 11/672,210

(22) Filed: Feb. 7, 2007

(65) Prior Publication Data

US 2007/0190521 A1 Aug. 16, 2007

Related U.S. Application Data

(60) Provisional application No. 60/772,790, filed on Feb. 13, 2006.

(51) Int. Cl.
| | |
|---|---|
| C12M 1/34 | (2006.01) |
| C12M 3/00 | (2006.01) |
| G01N 35/02 | (2006.01) |
| B01L 3/02 | (2006.01) |
| G01N 35/00 | (2006.01) |
| C12Q 1/00 | (2006.01) |
| G06K 9/00 | (2006.01) |

(52) U.S. Cl. .................. 435/287.1; 422/100; 435/4; 436/43; 436/47; 382/110

(58) Field of Classification Search ............... 435/287.1
See application file for complete search history.

(56) References Cited

U.S. PATENT DOCUMENTS 5,425,918 A 6/1995 Healey et al.

(Continued)

FOREIGN PATENT DOCUMENTS

EP 1 110 617 6/2001

(Continued)

OTHER PUBLICATIONS

Growth in Microtiter Plate, "System Duetz," 6 pages; http://www.enzyscreen.com/DB.html.

(Continued)

*Primary Examiner*—Jill Warden
*Assistant Examiner*—Jennifer Wecker
(74) *Attorney, Agent, or Firm*—James E. Davis; Joseph A. Schaper; Harness, Dickey & Pierce, P.L.C.

(57) ABSTRACT

The present disclosure generally relates to a high throughput system, apparatus, and methods useful for efficiently analyzing experimental liquid formulations applied to plants. In various embodiments, the high throughput system includes a liquid formulation dispensing subsystem (LFDS). The LFDS includes an automated moveable sample plate platform for holding at least one sample plate. Each sample plate includes a plurality of wells containing plant specimens. The LFDS is operable to sequentially position select ones of the wells at a well target location. Once a selected well is positioned at the target location, a micro-sprayer assembly, including at least one liquid formulation applicator, applies discrete amounts of a liquid formulation to the plant specimens within each selected well.

28 Claims, 12 Drawing Sheets

U.S. PATENT DOCUMENTS

| | | | |
|---|---|---|---|
| 6,269,757 B1 * | 8/2001 | Kiest | 111/119 |
| 6,739,518 B1 | 5/2004 | Davis et al. | |
| 6,803,205 B2 | 10/2004 | Duffy et al. | |
| 6,812,030 B2 | 11/2004 | Ozbal et al. | |
| 6,858,842 B2 | 2/2005 | Moon et al. | |
| 7,499,573 B2 * | 3/2009 | Tanabata et al. | 382/110 |
| 2002/0110920 A1 * | 8/2002 | Mentzen et al. | 436/104 |
| 2003/0136463 A1 * | 7/2003 | Zhou et al. | 141/129 |
| 2005/0058574 A1 * | 3/2005 | Bysouth et al. | 422/63 |
| 2006/0211132 A1 * | 9/2006 | Miledi et al. | 436/180 |

FOREIGN PATENT DOCUMENTS

| | | |
|---|---|---|
| EP | 1 564 542 | 8/2005 |
| WO | WO 00/79237 | 12/2000 |

OTHER PUBLICATIONS

Growth in Microtiter Plates, "System Duetz", 1 pages; http://www.enzyscreen.com/1555759.

* cited by examiner

HIGH THROUGHPUT SYSTEM AND METHODS FOR ANALYZING LIQUID FORMULATIONS

This application claims the benefit of U.S. Provisional Application No. 60/772,790, filed on Feb. 13, 2006. The disclosure of the above application is incorporated herein by reference.

FIELD

The present disclosure generally relates to apparatus and methods for a high throughput system for analyzing liquid formulations to be applied to plants.

BACKGROUND

To test the efficacy of liquid formulations applied to plants, e.g., herbicides and/or fertilizers, various experimental formulations are often applied to an array of planted seeds. The effectiveness of the formulations is then analyzed by tracking the effects of the formulation on the growth of the plants. Typically, experimental liquid formulations, such as herbicides and fertilizers, are tested in the greenhouse using standard plants. A visual assessment of formulation performance is made over time and formulations are ranked based on their performance compared to known standards. While the greenhouse assay is an effective tool to identify enhanced formulations, the number of formulations that can be analyzed per year is limited by the availability of greenhouse space, labor costs and time. Thus a need exists to facilitate the rapid and efficient analysis of experimental liquid formulations.

SUMMARY

There is now provided a high throughput system for efficiently analyzing experimental liquid formulations applied to plants. In various embodiments, the system includes a liquid formulation dispensing subsystem (LFDS). The LFDS includes an automated moveable sample plate platform for holding at least one sample plate. Each sample plate includes a plurality of wells, all or some of which may have a plant specimen therein. The LFDS is operable to sequentially position select ones of the wells at a well target location. Once a selected well is positioned at the target location, a micro-sprayer assembly, including at least one liquid formulation applicator, applies discrete amounts of a liquid formulation to the plant specimens within each selected well as the selected wells are sequentially positioned at the well target location.

There is further provided an automated method for assaying the effect of one or more liquid formulations on a plurality of plant specimens. In various embodiments, the method includes moving a sample plate platform supporting at least one sample plate including a plurality of wells to sequentially position selected ones of the wells at a well target location. Each selected well has therein a plant specimen. The method additionally includes operating a micro-sprayer assembly to apply discrete amounts of at least one liquid formulation to the plant specimens within each selected well as the selected wells are sequentially positioned at the well target location.

There is still further provided a liquid formulation dispensing system (LFDS) for applying one or more liquid formulations to a plurality of plant specimens. In various embodiments, the LFDS includes an automated moveable sample plate platform for holding at least one sample plate that includes a plurality of wells. The sample plate platform is moveable to sequentially position select ones of the wells at a well target location. Each selected well has therein a plant specimen. The LFDS additionally includes a micro-sprayer assembly that includes at least one liquid formulation applicator operable to apply discrete amounts of a liquid formulation to the plant specimens within each selected well as the selected wells are sequentially positioned at the well target location. The LFDS can further include an automated movable liquid formulation platform for supporting at least one vial rack. Each vial rack has placed therein a plurality of rows of vials, each containing a different one of a plurality of different liquid formulations. The liquid formulation platform is operable to sequentially position a plurality of selected rows of vials at the vial target location. The LFDS still further includes a formulation withdrawal assembly that includes a valve assembly having a plurality of uptake probes extending from a bottom edge. The formulation withdrawal assembly is operable to: insert each of the uptake probes into a respective one of the vials in the row of vials positioned at the target location; withdraw at least a portion of a selected one of the liquid formulation from the respective vial; and provide the withdrawn liquid formulation to the micro-sprayer assembly.

Still yet further there is provided an automated, high throughput method for analyzing herbicidal formulations. In various embodiments the method includes moving a liquid formulation platform supporting at least one vial rack having placed therein a plurality of rows of vials some or all of which may contain a different one of a plurality of different liquid formulations. The liquid formulation platform is automated to sequentially position a plurality of selected rows of vials at a vial target location. The method additionally includes operating a formulation withdrawal assembly that includes a valve assembly having a plurality of uptake probes extending from a bottom edge, to: sequentially insert each of the uptake probes into a respective one of the vials in each row of vials as the rows are sequentially positioned at the target location; withdraw at least a portion of a selected one of the liquid formulations from each row as the rows are sequentially positioned at the vial target location; and provide the withdrawn liquid formulations to a micro-sprayer assembly. The method further includes automatedly moving a sample plate platform, supporting at least one sample plate including a plurality of wells, in order to sequentially position selected ones of the wells at a well target location. Each well has therein a plant specimen. The method still further includes operating a micro-sprayer assembly to apply discrete amounts of at least one liquid formulation to the plant specimens within each selected well as the selected wells are sequentially positioned at the well target location.

The present disclosure provides a high throughput system, apparatus and methods to overcome the disadvantages of the current method used to test experimental herbicidal formulations. The present disclosure facilitates the rapid and efficient analysis of experimental herbicidal formulations by allowing chemists to use a combinatorial approach to the development of new formulations. This allows novel combinations of surfactants and formulation additives to be analyzed rapidly with a minimum of space and labor requirements. These and other features and advantages will be in part apparent, and in part pointed out hereinafter.

BRIEF DESCRIPTION OF THE DRAWINGS

Corresponding reference numerals indicate corresponding parts throughout the several views of the drawings.

DETAILED DESCRIPTION

This detailed description is intended only to acquaint others skilled in the art with Applicants' disclosure, its principles, and its practical application so that others skilled in the art may adapt and apply the disclosure in its numerous forms, as such forms may be best suited to the requirements of a particular use. This description and its specific examples are intended for purposes of illustration only. This disclosure, therefore, is not limited to the embodiments described in this application, and may be variously modified.

Figure 1:
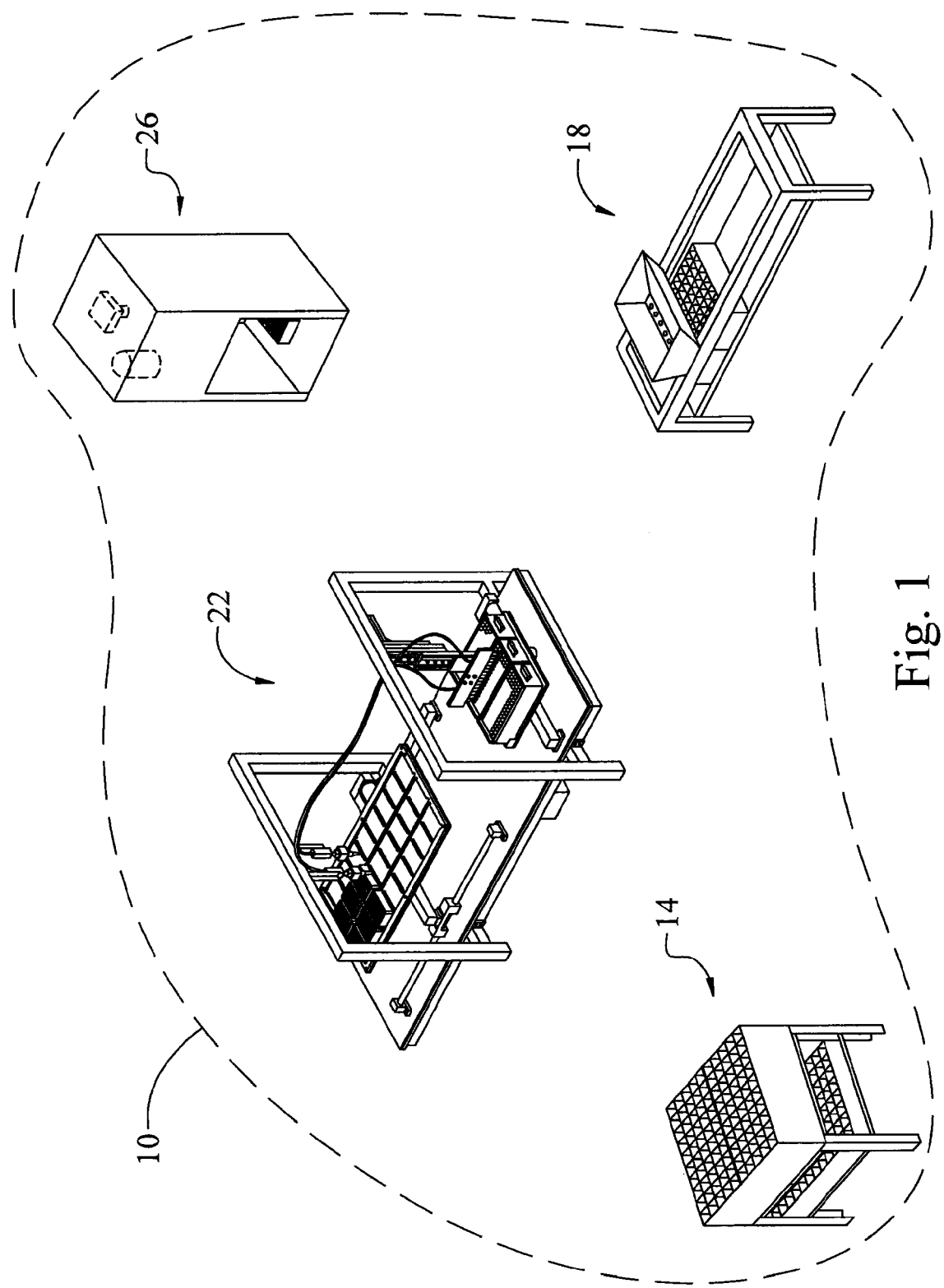
FIG. 1 is schematic of a high throughput liquid formulation analysis (HTLFA) system for rapidly analyzing experimental liquid formulations applied to plants, in accordance with various embodiments of the present disclosure.

Referring to FIG. 1, a high throughput liquid formulation analysis (HTLFA) system 10 for more efficiently analyzing large numbers of experimental liquid formulations applied to plants is provided, in accordance with various embodiments of the present disclosure. The HTLFA system 10 can be used to analyze a wide variety of formulations applied to plants including, for example, herbicidal and fertilizer formulations. Generally, the HTLFA system 10 includes a soil jig 14, a seed dispensing device 18, a liquid formulation dispensing subsystem (LFDS) 22 and an imaging system 26.

Figure 2:
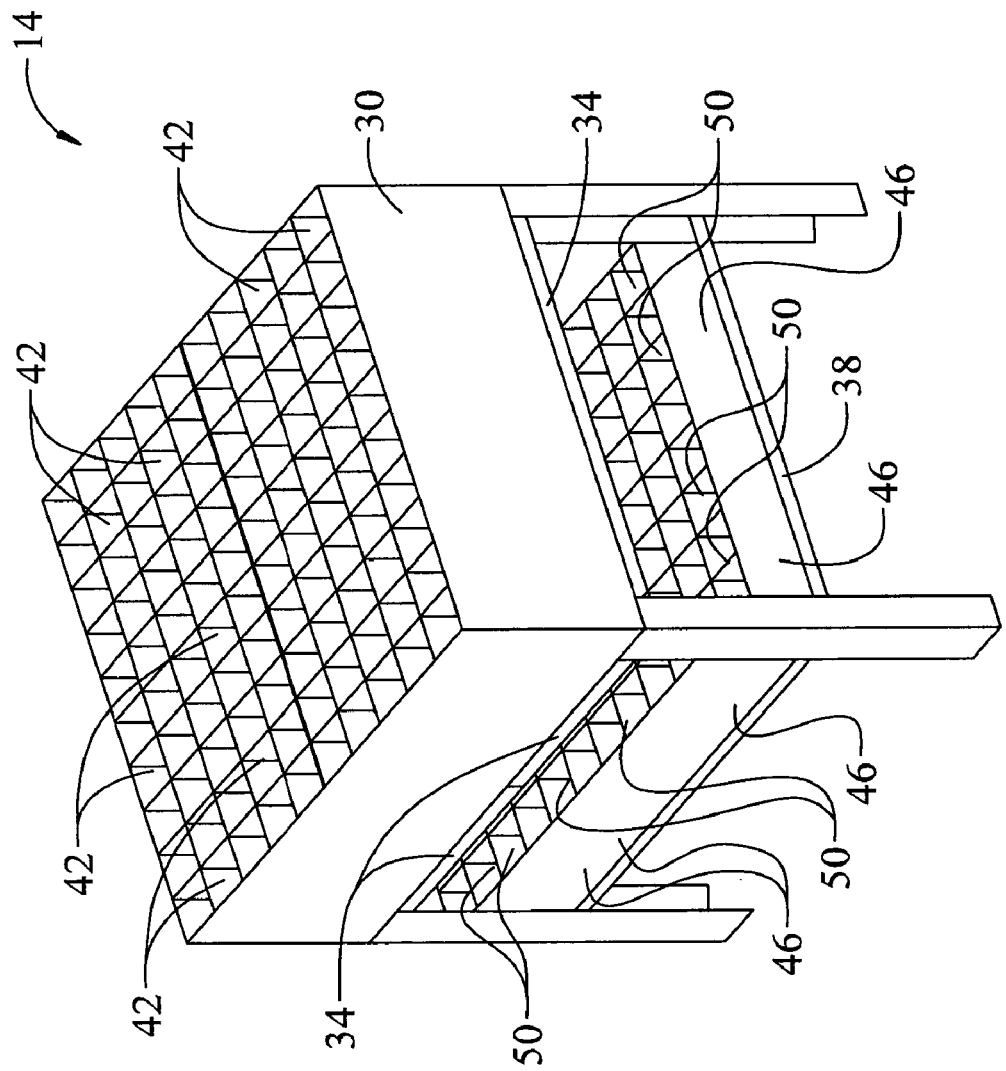
FIG. 2 is an isometric view of an exemplary soil jig included in the HTLFA system shown in FIG. 1, in accordance with various embodiments of the present disclosure.

FIG. 2 provides an exemplary illustration of the soil jig 14, in accordance with various embodiments of the present disclosure. The soil jig 14 can be any delivery device suitable for delivering a fixed amount of soil or other plant growth medium to each of a plurality of wells in a sample plate (described further below). For example, in various embodiments, the soil jig 14 includes a main body 30, at least one soil release door 34 and a sample plate platform 38. The main body 30 includes a plurality of soil bins 42 into which a suitable soil or other growth medium for planting a test subject plant can be deposited. Although the soil jig 14 can include more than one soil release door 34, for simplicity, the description herein will refer to the one or more soil release doors in the singular, i.e., simply as the release door 34. The release door 34 is moveable between a closed and open position. In the closed position, the release door 34 covers a bottom of the main body 30 and substantially seals a bottom of each soil bin 42. When moved to the open position, the release door 34 exposes the bottom of each soil bin 42. In operation, the release door 34 is placed in the closed position and each soil bin 42 is slightly overfilled with soil. Any suitable soil or other medium for plant growth may be used. The top of the main body 30 is then scraped or razed with a trowel device (not shown) so that each soil bin 42 is completely filled and contains substantially the same amount of material, for example, 2.5 ml of soil. One or more sample plates 46 including a plurality of wells 50 is/are placed on the sample plate platform 38 beneath the main body 30 and release door 34.

The multi-well sample plates 46 can be any sample plate comprising a plurality of sample wells suitable for retaining soil or another medium in which plants are grown for analyzing the effects of various experimental liquid formulations applied to the plants. For example, in various embodiments, each sample plate 46 can be a polypropylene microtitre plate including any desirable number of sample wells 50, such as 96 wells, 384 wells or other the like. An example of a suitable sample plate 46 is a commercially available 2 ml, 96-well, polypropylene, round bottom microtitre plate produced by Whatman Inc. of Clifton, N.J.

Each sample plate 46 is positioned on the sample plate platform 38 such that each of the wells 50 is aligned beneath one of the soil bins 42. The release door can then be moved to the open position to release the soil or other growth medium from each soil bin 42 allowing the soil or growth medium to fall into the corresponding aligned sample well 50. Thus, the soil jig 14 delivers a uniform volume of soil or growth medium to each well 50 in each sample plate 46 and enables rapid preparation of the sample plates 50 for seeding, as described below. Additionally, in various embodiments, each well 50 can have at least one drainage hole in the bottom to allow for watering by sub-irrigation.

Figure 3:
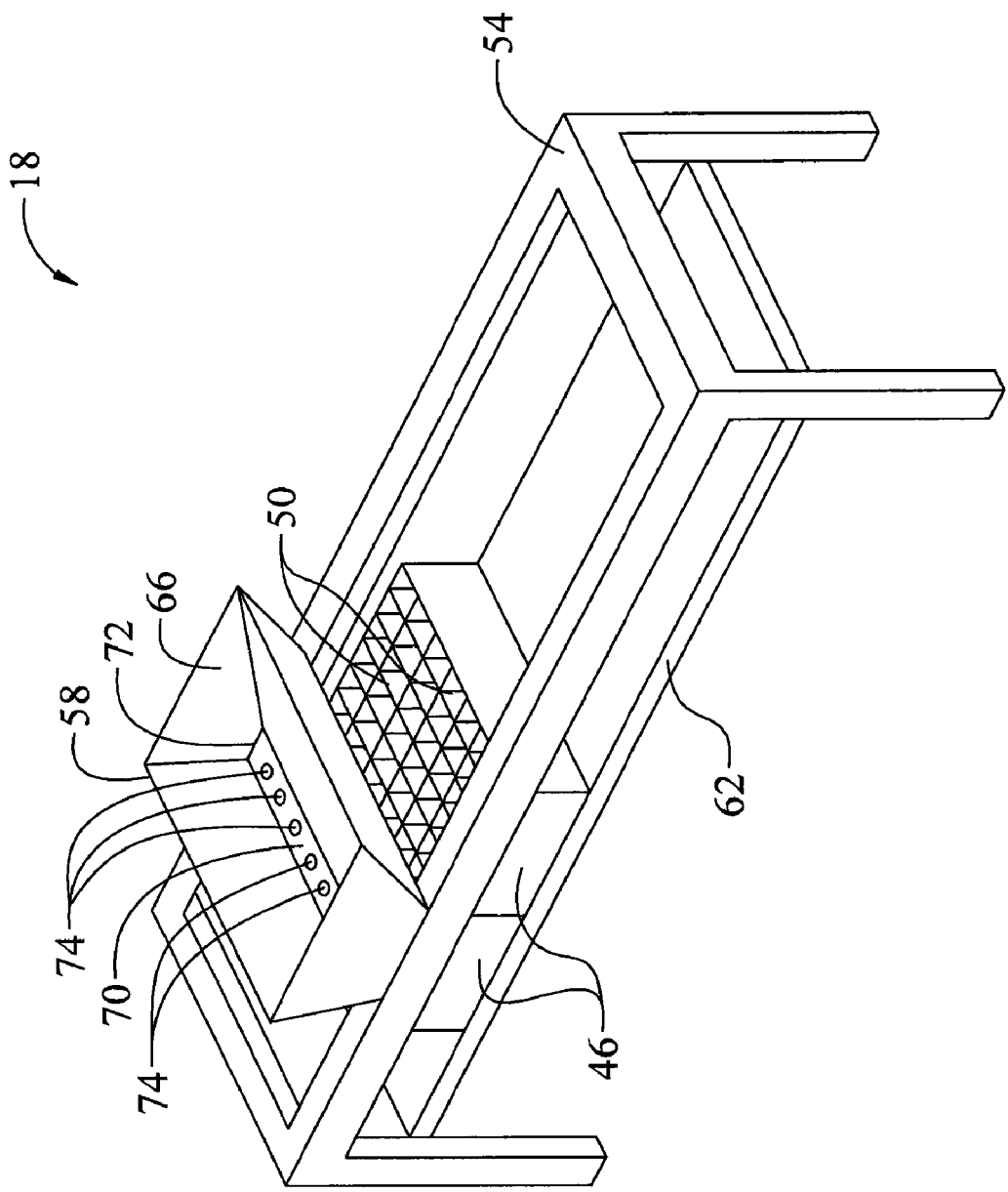
FIG. 3 is an isometric view of an exemplary seed dispensing device included in the HTLFA system shown in FIG. 1, in accordance with various embodiments of the present disclosure.

Referring now to FIG. 3, the seed dispensing device 18 is structured to allow seeding of multiple plants in an efficient manner by quickly delivering, or depositing, a controlled amount of seed, e.g., a substantially consistent amount of seed, into each well 50 filled with soil or other growth medium in each of one or more sample plates 46. In various embodiments, the seed dispensing device 18 includes a frame 54, a seed dispenser 58 for dispensing and depositing seeds into the soil filled wells 50 of one or more sample plates 46 positioned on a sample plate platform 62 beneath the seed dispenser 58. The seed dispenser 58 is movable along a length of the frame 54 so that the seed dispenser 58 can be placed above any one or more of the plurality of sample plates 46 positioned on the sample plate platform 62. Once the seed dispenser 58 is properly positioned above one or more of the sample plates 46, the seed dispenser 58 can be operated to dispense a substantially consistent amount of seed into each well 50 in a row of one or more sample plates 46.

Generally, the seed dispenser includes a hopper 66 and an elongated seed dispensing body 70 axially aligned with a longitudinal opening 72 formed at the bottom of the hopper 66. The elongated seed dispensing body 70 includes a plurality of cavities 74 spaced along the length of the elongated seed dispensing body 70 for receiving seed therein. The hopper 66 can be filled with seed such that each cavity 74 is filled with substantially the same amount of seed. Once the seed dispenser 58 is properly positioned above one or more of the sample plates 46, the elongated seed dispensing body 70 can be operated to dispense the seed within each cavity into a corresponding well 50 of a row of one or more sample plates 46.

More specifically, in various embodiments, the elongated seed dispensing body 70 comprises a seed dispensing rod, referred to herein as seed dispensing rod 70 rotationally mounted below, and axially aligned with the longitudinal opening 72. The dispensing rod 70 includes a plurality of depressions, or cavities, 74 equally spaced along the length of the dispensing rod 70. Particularly, the spacing of the depressions 74 along the length of the dispensing rod 70 is substantially equal to the spacing between the centers of each well 50 of a row in at least one sample plate 46. Thus, each depression 74 corresponds to an individual well 50 of a row in at least one sample plate 46. Additionally, the depressions 74 are sized to accommodate a specified amount of a particular seed. For example, each depression 74 can be sized to hold 1-3 tobacco seeds.

To deposit seeds into each of the sample wells 50, the hopper is filled with seed, e.g., tobacco seed. Accordingly, each depression 74 is filled with the predetermined amount of seed, e.g., 1-3 seeds. The hopper 66 is then positioned over one or more sample plates 46 such that the dispensing rod 70 longitudinally aligns with a row of wells 50 of the respective sample plate(s) 46. The dispensing rod 70 can then be rotated such that the seed falls out of the depressions 74 and is deposited into the corresponding wells 50. Thus, the seed dispensing device 18 efficiently delivers a substantially consistent amount of seed to the wells 50 in multiple sample plates 46, thereby providing uniformity in the plant area of each well 50.

Figure 4:
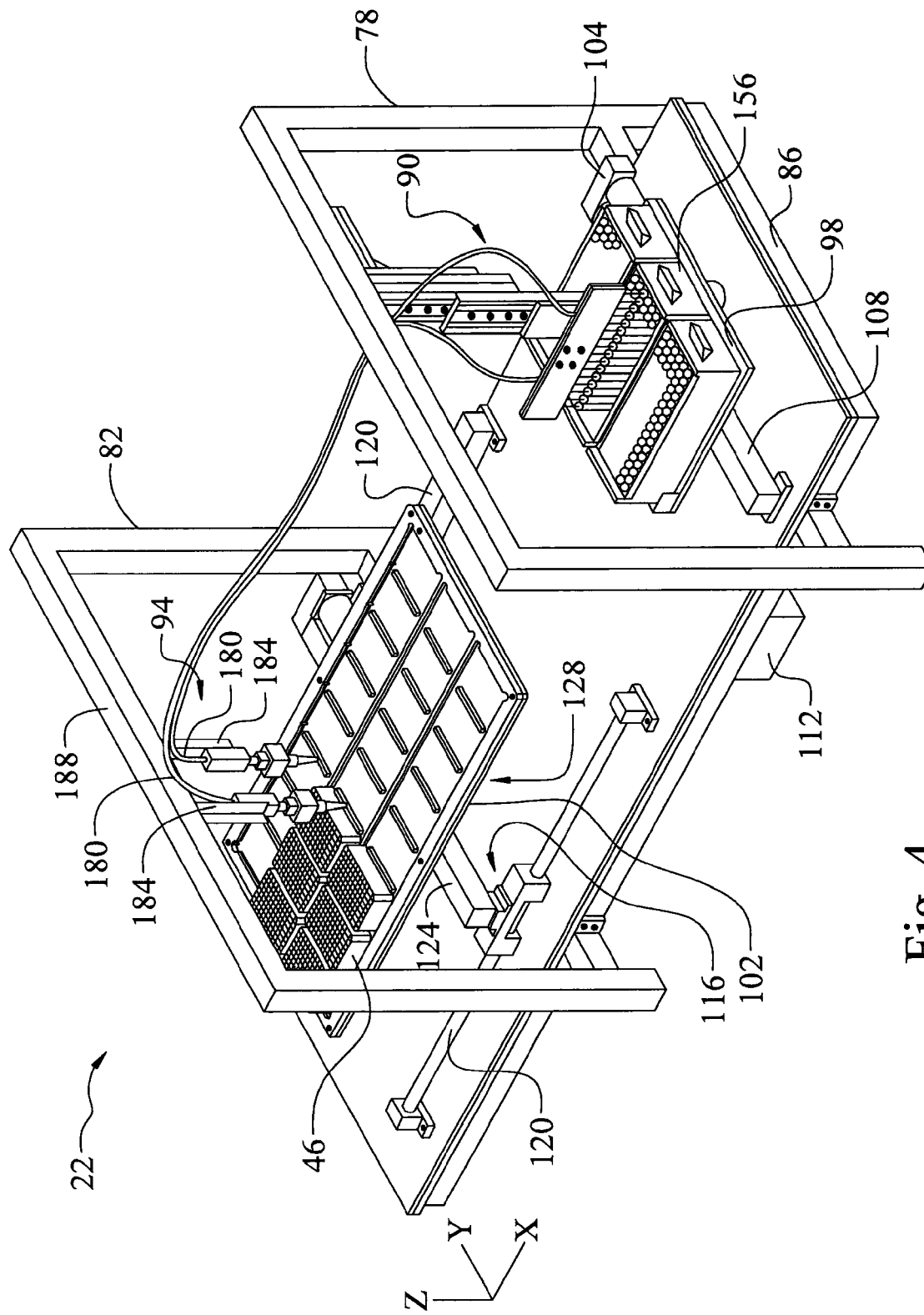
FIG. 4 is an isometric view of an exemplary a liquid formulation dispensing subsystem (LFDS) included in the HTLFA system shown in FIG. 1, in accordance with various embodiments of the present disclosure.
Figure 5:
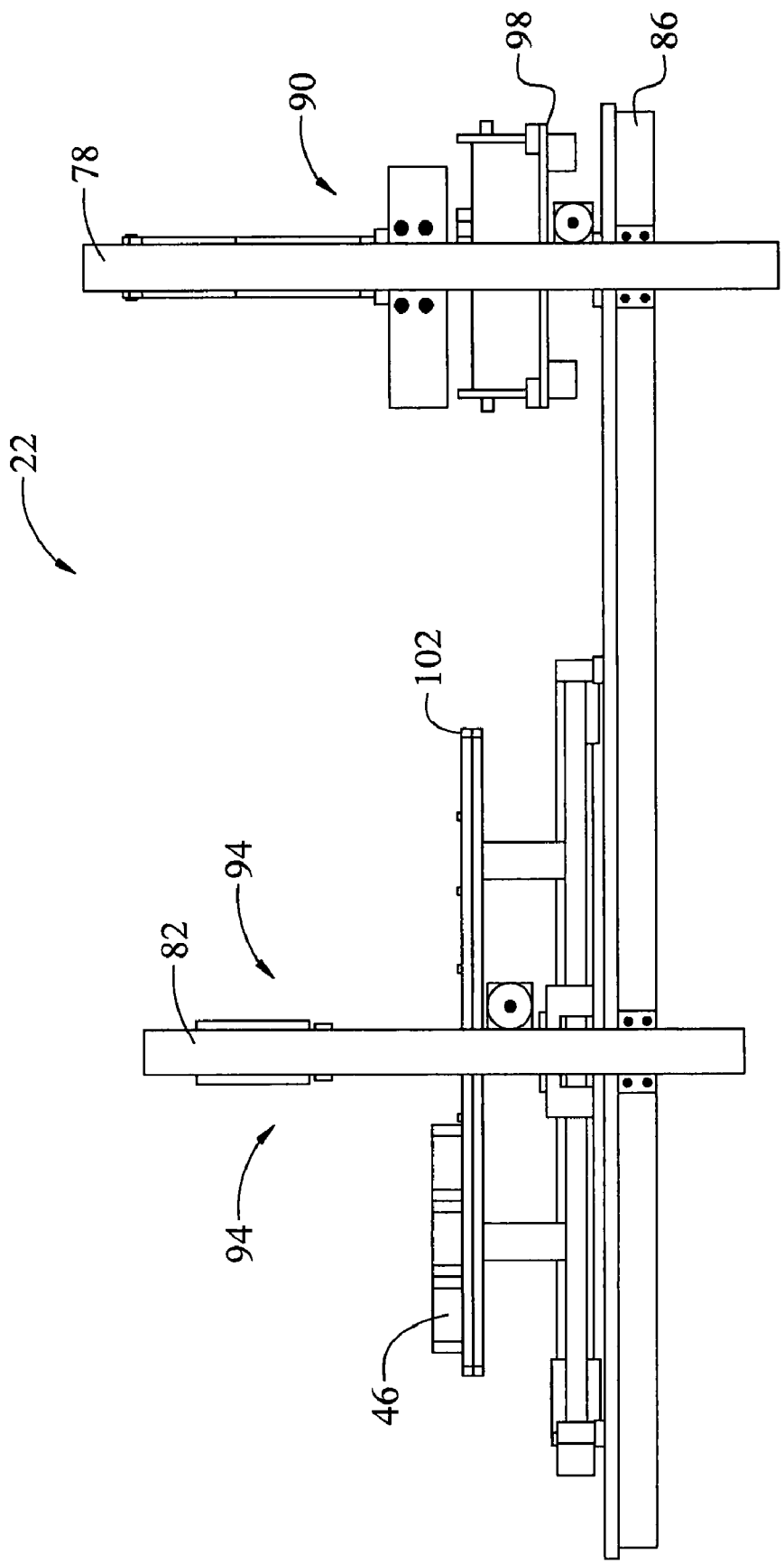
FIG. 5 is a side view of the LFDS shown in FIG. 4, in accordance with various embodiments of the present disclosure.

Referring now to FIGS. 4 and 5, the LFDS 22 provides the rapid selection and application of a plurality of liquid formulations to a plurality of plant test samples planted in the wells 50 of the sample plates 46. The plant test samples can be planted in the sample plates 46 using any suitable means or process. For example, in various implementations the plant test samples can be planted in the sample plates 46 using the soil jig 14 and the seed dispensing device 18, as described above. The LFDS 22 includes a formulation withdrawal assembly support structure 78, a micro-sprayer assembly support structure 82 and a base frame 86. The liquid formulation dispensing subsystem additionally includes a formulation withdrawal assembly 90, a micro-sprayer assembly 94, a movable liquid formulation platform 98 and a moveable sample plate platform 102.

The moveable liquid formulation platform 98 is mounted on a Y-axis translation stage 104 that is controllable to bi-directionally move the liquid formulation platform 98 along a track 108 of the translation stage 104. In various embodiments, operation of the Y-axis translation stage 104, as well as various other automated systems, sub-systems, assemblies, subassemblies, mechanisms, and/or devices of the LFDS 22 are controlled by a liquid formulation dispensing subsystem (LFDS) controller 112.

The LFDS controller 112 can be any suitable computer based control system including such elements as a processor, memory and various other electronic control elements known by those skilled in the art to be utilized in automated control, e.g., robotic control, systems. In various embodiments, the LFDS controller comprises a forward control computer that has associated with it the motion routines and processes for controlling the overall operation and function of the LFDS 22 system. In various other embodiments, the LFDS controller 112 can be communicatively connected to a remote host computer system (not shown). The remote host computer system can generate and retain various databases and/or tables that include various data, routines and programs utilized and executed by the LFDS controller 112 to control the overall operation and function of the LFDS 22 system. The remote host computer system can also run a Laboratory Information System to track the various experimental liquid formulations used and the logistics of which well 50 of each sample plate 46 was sprayed with each specific experimental liquid formulation.

In various embodiments, the moveable sample plate platform 102 is mounted on a translation stage 116 that is controllable to bi-directionally move the sample plate platform 102 in the X and Y directions along a pair of X-axis tracks 120 and a Y-axis track 124 of the X-Y stage 116. In various other embodiments, the translation stage 116 is controllable to bi-directionally move the sample plate platform 102 in the X, Y and Z directions along the X-axis track 120, the Y-axis track 124 and a Z-axis lift device, generally indicated at 128. In various implementations, operation of the translation stage 116 is controlled by the LFDS controller 112.

Figure 6:
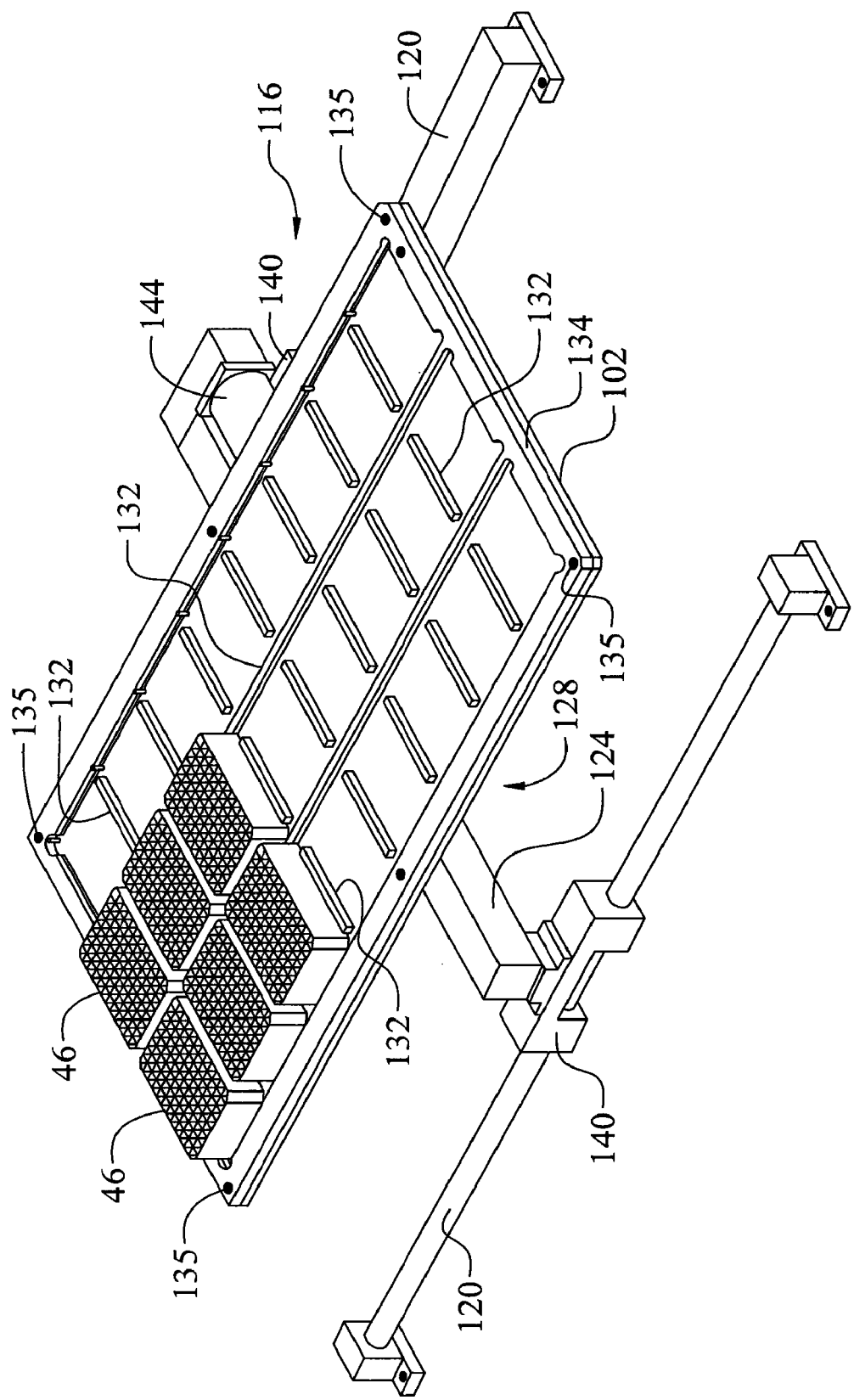
FIG. 6 is an enlarged isometric view of a moveable sample plate platform and a translation stage of the LFDS shown in FIG. 4, in accordance with various embodiments of the present disclosure.
Figure 7:
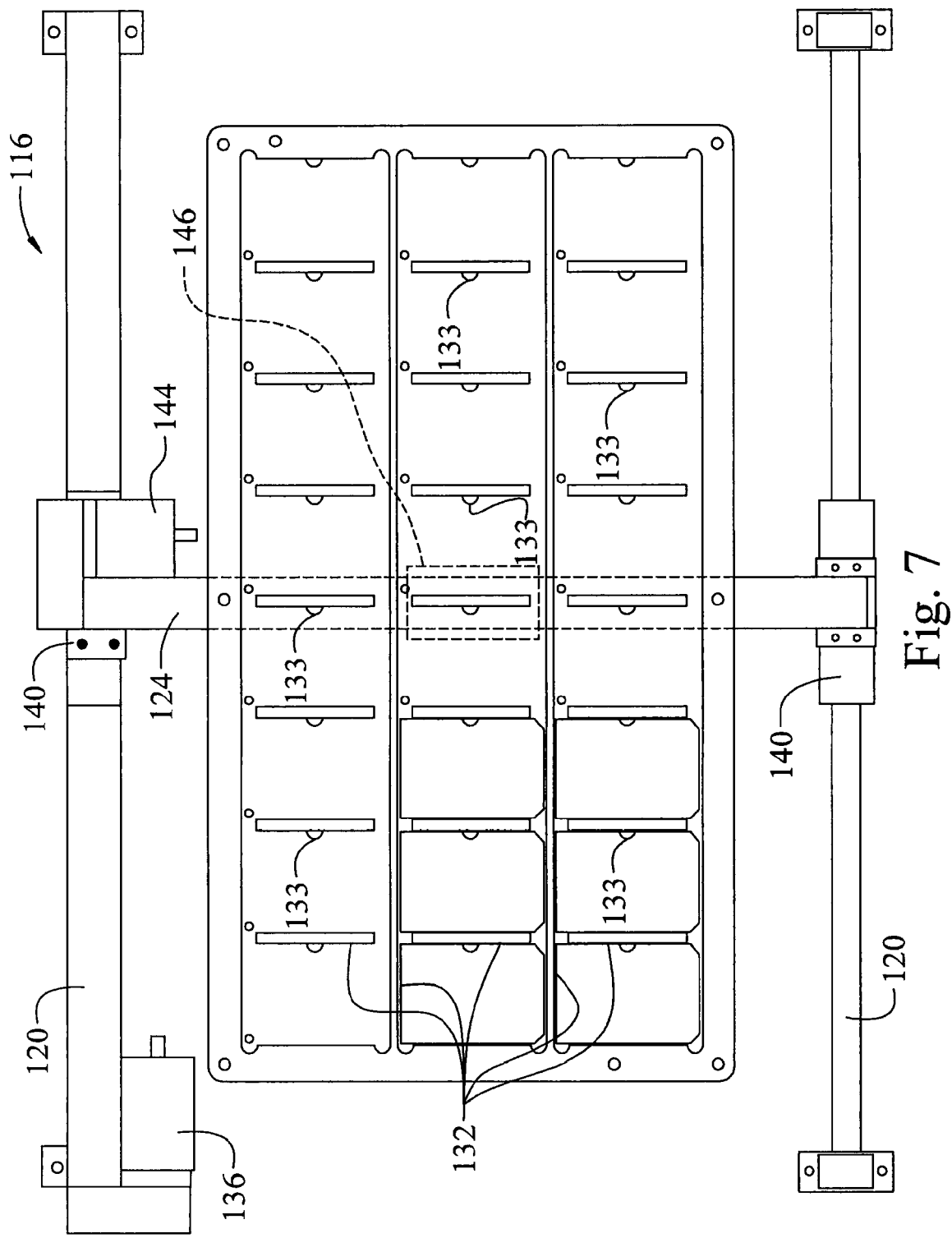
FIG. 7 is a top plan view of the moveable sample plate platform and the translation stage of the LFDS shown in FIG. 4, in accordance with various embodiments of the present disclosure.

Referring also to FIGS. 6 and 7, the moveable sample plate platform 102 is structured to securely retain a plurality of sample plates 46 in fixed positions and orientation. For example, the sample plate platform 102 can include a plurality of raised ridges 132 that securely hold each sample plate 46 in a fixed position and orientation. The sample plate platform 102 is capable of holding a plurality of sample plates 46 placed on the sample plate platform 102 in any arrangement. For example, in particular embodiments, the sample plate platform 102 is structured to hold twenty-four individual sample plates 46 arranged in a three by eight matrix. In various embodiments, selected ones of the raised ridges 132 include a key 133, shown in FIG. 7, that mates with a recess (not shown) in each of the sample plates 46. Therefore, each sample plate 46 is properly oriented on the sample plate platform 102 and each well 50 of each sample plate 46 can be consistently identified and tracked throughout use of the HTLFA system 10.

In other embodiments, as best illustrated in FIG. 6, a sample plate tray 134 is removably connectable to the sample plate platform 102. In such embodiments, the sample plate tray 134 includes the raised ridges 132 to securely hold each sample plate 46 in a fixed position and orientation. Furthermore, in such embodiments, the sample plate tray 134 and the sample plate platform 102 are structured to be removably connectable with each other using a fastening device exemplarily illustrated at 135. The fastening devices 135 can be any suitable fastening device for removably securing the sample plate tray 134 to the sample plate platform 102 and maintaining the sample plate tray 134 in a desired orientation with respect to the translation stage 116. For example, in various embodiments, the fastening devices 135 can be screws, snaps, rivets, locating pins, latches, various interlocking snap fit fasteners, etc.

As described above with reference to FIGS. 2 and 3, each of the sample plates 46 comprises a plurality of wells 50 for receiving soil and at least one plant seed to cultivate at least one plant. The sample plates 46 can have any number of wells 50 in any arrangement. In various embodiments, the wells 50 are arranged in a plurality of synonymous columns and rows. The sample plates 46 can be constructed of polypropylene, styrene, or any other suitable material. In various embodiments the sample plates 46 are translucent to facilitate imaging of the cultivated plants, as further described below. In various embodiments, the sample plates 46 comprise a 96-well or 384-well configuration. An example of a suitable plate includes a commercially available 2 ml, 96-well, polypropylene, round bottom microtitre plate (Whatman Inc. Clifton, N.J.). Additionally, in various embodiments, the sample plates 46 have at least one drainage hole in the bottom of each well 50 to allow for watering of the cultivated plant by sub-irrigation.

In various embodiments, exemplarily illustrated in FIGS. 6 and 7, the translation stage 116 includes a first linear actuator 136 that controls movement of a first translatable carriage 140 slidingly mounted on one of the X-axis tracks 120, and a second linear actuator 144 that controls movement of a second translatable carriage 146 (shown in phantom in FIG. 7) slidingly mounted on the Y-axis track 124. The Y-axis track 124, having the second linear actuator 144 and the second translatable carriage 146 mounted thereto, is mounted on the first translatable carriage 140. Additionally, the sample plate platform 102 is mounted on the second translatable carriage 146. Thus, in various embodiments, the sample plate platform 102 can be precisely bi-directionally moved in two dimensions, e.g., the X and Y directions, through the operation of the first and second linear actuators 136 and 140. In various other embodiments, the second translatable carriage 146 can have the Z-axis lift device 128, e.g., a linear actuator, mounted thereto to additionally provide precise movement of the sample plate platform in the Z-direction.

Figure 8:
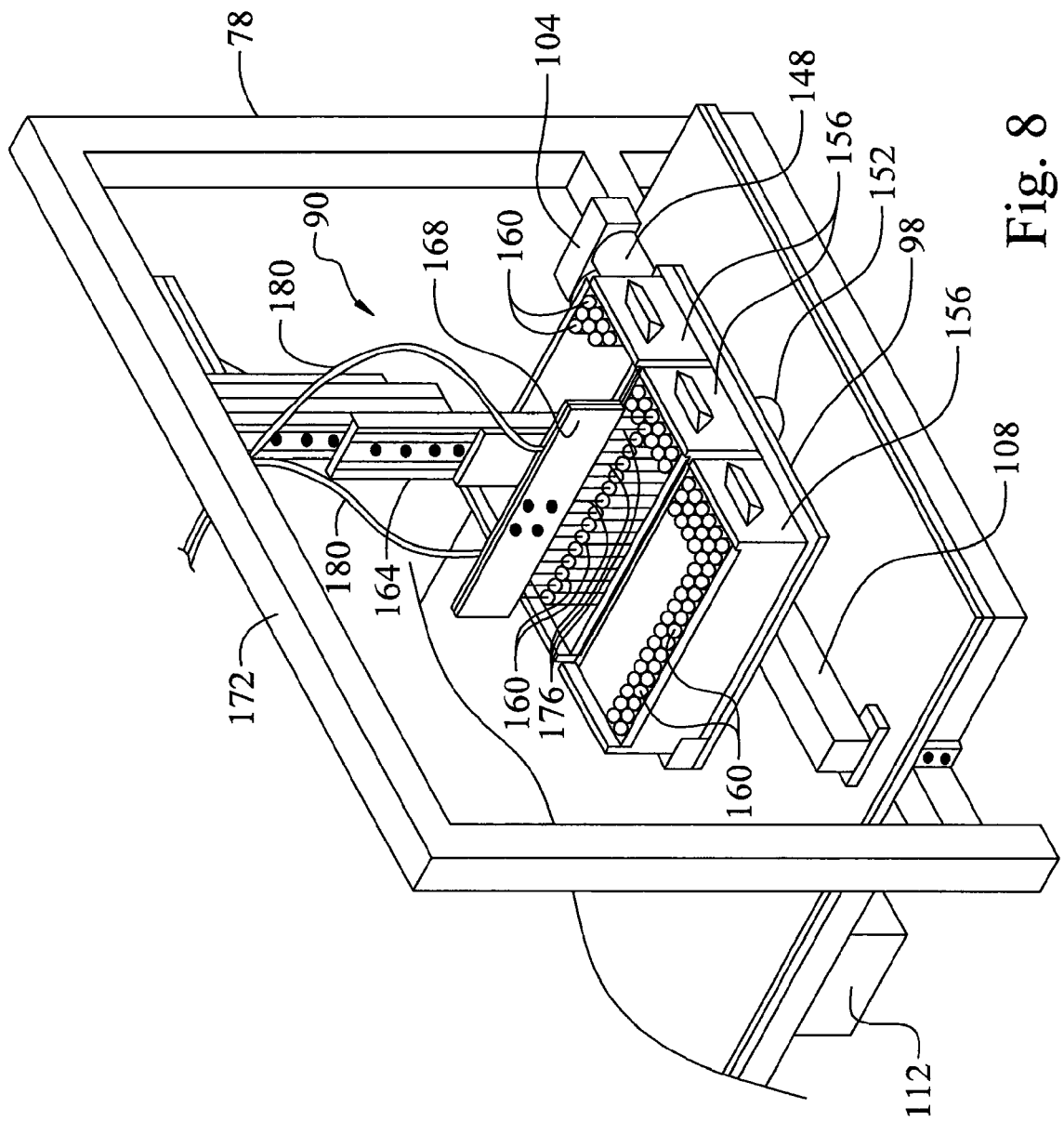
FIG. 8 is a sectional isometric view of a liquid formulation withdrawal assembly included in the LFDS shown in FIG. 4, in accordance with various embodiments of the present disclosure.

Referring now to FIG. 8, the Y-axis translation stage 104 connected to the moveable liquid formulation platform 98 further includes a third linear actuator 148 that controls movement of a third translatable carriage 152 slidingly mounted on the Y-axis track 108. Thus, in various embodiments, the liquid formulation platform 98 can be precisely moved bi-directionally along the Y-axis track 108, through the operation of the third linear actuator 148. More specifically, the liquid formulation platform 98 is structured to support and retain one or more liquid formulation vial racks 156 in a desired position and orientation. Although FIG. 8 exemplarily illustrates the liquid formulation platform 98 retaining three vial racks 156, the scope of the present disclosure should not be so limited. In various embodiments, the liquid formulation platform 98 can be structured to support and retain less than or more than three liquid formulation vial racks 156 in a desired position and orientation.

Each vial rack 156 holds a plurality of rows of vials 160 in which various experimental liquid formulations are placed to be tested and analyzed using the LFDS 22, as described herein. The vial racks 156 can be structured to hold any number and size of vials 160. For example, in various embodiments, each vial rack 156 holds 128 vials arranged in a sixteen by eight array of vials measuring 13 mm by 100 mm. Therefore, in such embodiments, if three vial racks 156 are utilized, 384 different experimental liquid formulations can be analyzed at any one time. For clarity and simplicity, the vial racks 156 shown in FIG. 8 are shown only partially filled with vials 160. However, it should be understood that in operation each vial rack 156 would be filled with completed rows of vials 160, in which all or some of the vials 160 could contain an experimental liquid formulation. Thus, the liquid formulation platform 98 can be moved bi-directionally along the Y-axis track 108 to accurately position a specific row of vials 160 at a target location directly under the liquid formulation withdrawal assembly 90, as described below.

In various embodiments, the liquid formulation withdrawal assembly 90 includes formulation uptake vertical position device 164 having a valve assembly 168 mounted at a distal end. The formulation uptake vertical position device 164 is suspended above the liquid formulation platform 98, from a cross bar 172 of the formulation withdrawal assembly support structure 78. The formulation uptake vertical position device 164 can be any device suitable to controllably raise and lower the multi-port valve assembly 168 along the Z-axis. For example, the formulation uptake vertical position device 164 can be a pneumatically controlled interlocking track device, or a pneumatically controlled piston device, etc.

The valve assembly 168 includes a plurality of uptake probes 176 extending along a bottom of the valve assembly 168 downward toward the liquid formulation platform 98. The valve assembly 168 additionally includes one or more feed tubes 180 extending from a top of the multi-port valve assembly 168 and attached to the cross bar 172. Furthermore, the valve assembly 168 is communicatively connected to a vacuum source (not shown) that selectively provides a vacuum to each of the uptake probes 176, as controlled by the valve assembly 168. Further yet, the valve assembly 168 is mounted to the formulation uptake vertical position device 164 such that a longitudinal axis of the valve assembly 168 is parallel with the longitudinal axes of the vial racks 156. Therefore, the liquid formulation platform 98 can be positioned under the valve assembly 168 such that a specific longitudinal row of vials 160 is positioned at the target location, i.e., the specific longitudinal row of vials 160 is aligned directly beneath the row of uptake probes 176 with each uptake probe 176 aligning with a respective one of the vials 160.

In operation, the LFDS controller 112 moves the liquid formulation platform 98 along the Y-axis translation stage track 108 to position a particular longitudinal row of vials 160 at the target location directly beneath the row of uptake probes 176. The LFDS controller 112 then lowers, or extends, the formulation uptake vertical position device 164 so that each uptake probe is inserted into the corresponding aligned vial 160. The LFDS controller 112 then operates the valve assembly 168 to select and withdraw the experimental liquid formulation from a specific one of the vials 160 via the respective uptake probe 176. The withdrawn experimental liquid formulation is then fed through the feed tube 180 to micro-sprayer assembly 94, where the experimental liquid formulation is applied to the planted specimens in various randomly selected wells 50 of various randomly selected sample plates 46, as described below. The random selection of the wells 50 and the sample plates 46 is implemented to overcome the effects of well-to-well variations.

Once the micro-sprayer assembly 94 has dispensed the selected experimental liquid formulation on the various randomly selected sample wells 50, the LFDS controller 112 selects a subsequent experimental liquid formulation to be dispensed by the micro-sprayer assembly 94. The LFDS controller 112 can operate the valve assembly 168 to select and withdraw a subsequent experimental liquid formulation from a different vial 160 in the same longitudinal row of vials 160. Or, the LFDS can raise, or retract, the formulation uptake vertical position device 164 to withdraw all the uptake probes 176 from the respective vials 160. The Y-axis translation stage 104 can then be operated to move the formulation platform 98 along the track 108 to position a different longitudinal row of vials 160 at the target location directly beneath the row of uptake probes 176. The formulation uptake vertical position device 164 can then be operated to lower the uptake probes 176 into the subsequently selected row of vials 160 to select and withdraw a subsequent experimental liquid formulation from a specific one of the vials 160, as described above. The process of raising the valve assembly 168 and uptake probes 176, moving the racks 156 of vials 160, then lowering the probes 176 into the vial to select and withdraw a selected liquid formulation, can be repeated until each well 50 of each sample plate 46 loaded on the sample plate platform 102 has been sprayed with a selected liquid formulation.

In various embodiments, the valve assembly 168 is a multi-port valve assembly such that the experimental liquid formulation withdrawn from the vials 160 by a first half of the uptake probes 176 is fed to a first feed tube 180, while the experimental liquid formulation withdrawn from the vials 160 by a second half of the uptake probes 176 is fed to a second feed tube 180. Additionally, in various embodiments, the feed tube(s) 180 comprise low-volume flexible tubing. Also, in various embodiments, each longitudinal row of vials 160 can be replaced with a trough-like vessel that can be filled with a single experimental liquid formulation. Therefore, all of the uptake probes 176 would be inserted into a single, common experimental liquid formulation when the formulation uptake vertical position device 164 lowers the valve assembly 168.

Figure 9:
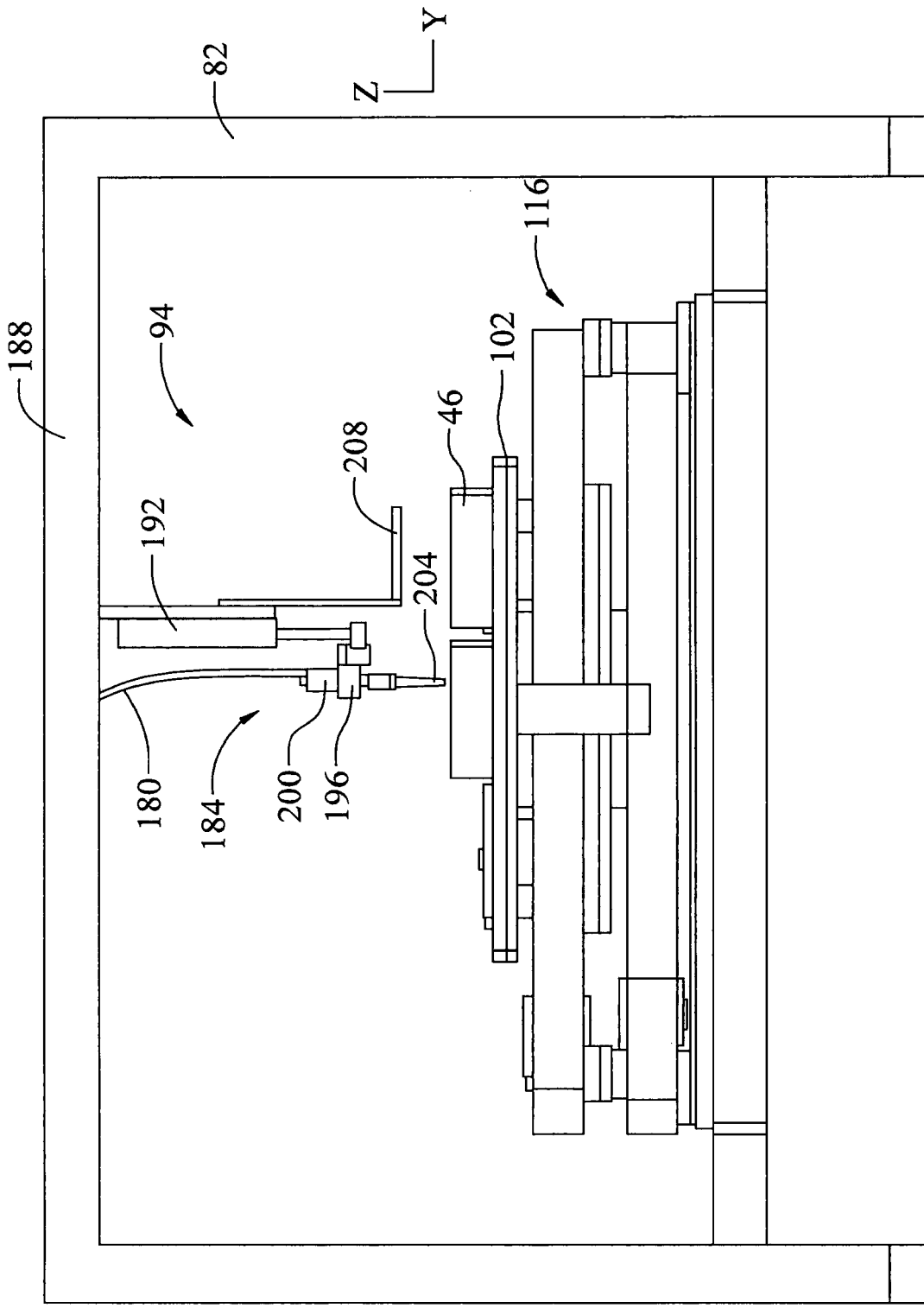
FIG. 9 is a rear view of a micro-sprayer assembly included in the LFDS shown in FIG. 4, in accordance with various embodiments of the present disclosure.
Figure 10:
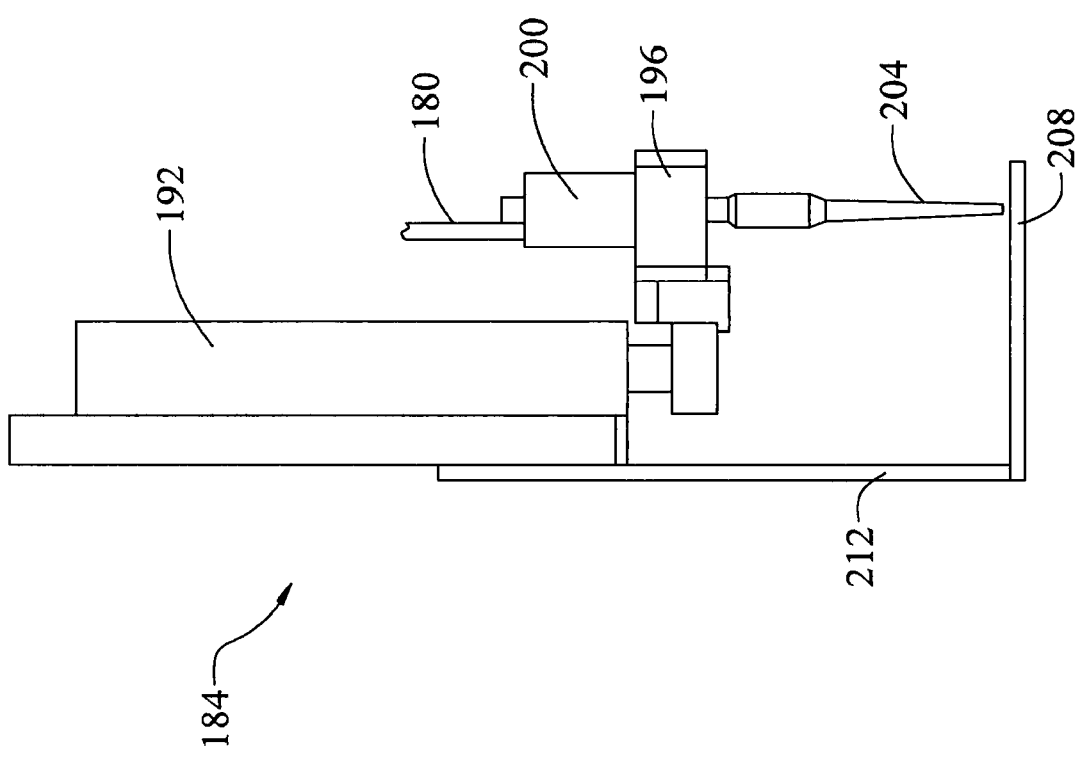
FIG. 10 is an enlarged side view of a liquid formulation applicator of the micro-sprayer assembly shown in FIG. 9, in accordance with various embodiments of the present disclosure.

Referring now to FIGS. 9 and 10, as described above, the LFDS 22 further includes the micro-sprayer assembly 94 that receives the selected experimental liquid formulation withdrawn by the liquid formulation withdrawal assembly 90, as described above. More specifically, the micro-sprayer assembly 94 functions to apply discrete amounts of the selected experimental liquid formulation to at least one plant specimen when the respective sample plate 46 is moved, via the translation stage 116, to a spray position, as described further below. The micro-sprayer assembly 94 includes at least one liquid formulation applicator 184 suspended above the sample plate platform 102, from a cross bar 188 of the micro-sprayer assembly support structure 82. Each liquid formulation applicator 184 includes a dispensing vertical position device 192 that bi-directionally moves a micro-spraying sub-assembly 196 up and down along the Z-axis. The dispensing vertical position device 192 can be any device suitable to controllably raise and lower the micro-spraying subassembly 196 along the Z-axis. For example, the dispensing vertical position device 164 can be a pneumatically controlled interlocking track device, or a pneumatically controlled piston device, etc.

The micro-spraying subassembly 196 includes a fluid metering pump 200 that receives the selected liquid formulation, via the feed tube 180, and dispenses a precisely metered amount of the selected liquid formulation to a selected sample well 50, via a spraying nozzle 204. The precision of the metering pump 200 in combination with the spraying nozzle 204 allows the micro-spraying subassembly 196 to accurately deliver very small amounts, e.g., micro-liter amounts, of the selected liquid formulation to each selected well 50. In various embodiments, the spraying nozzle 204 is an ultrasonic spraying nozzle. The metering pump 200 is controlled by the LFDS controller 112 to dispense any selected amount of the selected liquid formulation. More particularly, as the micro-spraying subassembly dispenses a selected liquid formulation to randomly selected sample wells 50, as described below, the amount dispensed to each well 50 can vary in accordance with commands from the LFDS controller 112. Thus, the metering pump 200 can dispense a first amount of the selected liquid formulation to a first sample well 50, then immediately dispense a different second amount of the selected liquid formulation to a second sample well 50 positioned under the spray nozzle 204, as described below.

In various embodiments, each liquid formulation applicator 184 additionally includes a movable fluid dump drain 208. The dump drain 208 is pivotal about a spindle 212 such that the dump drain 208 can be moved between a deployed position, shown in FIG. 10, and a stowed position, shown in FIG. 9. In the deployed position, the dump drain 208 is positioned directly under the spray nozzle 204. When the dump drain 208 is moved to the deployed position, the metering pump 200 can pump a second selected liquid formulation through the spray nozzle 204 to flush the spray nozzle 204 and feed tube 180. The flushed fluid is collected by the dump drain 208 and discarded to a waste container (not shown). This flushing process cleanses the feed tube 180 and spray nozzle 204 of a previously selected experimental liquid formulation so that a subsequently selected experimental liquid formulation will not be contaminated. In the stowed position, the dump drain 208 is positioned away from the nozzle 204, e.g., 180° from the deployed position. Particularly, in the stowed position, the dump drain 208 is positioned to allow the dispensing vertical position device 192 to lower, or extend, the spray nozzle 204 into a selected sample well 50 positioned, by operation of the translation stage 116, at a target location. The target location being directly beneath the spray nozzle 204.

In operation, the LFDS controller 112 controls operation of the translation stage 116 to position a selected well 50 of the one or more sample plates 46 on the sample plate platform 102 at the target location, i.e., directly under the spray nozzle 204. The LFDS controller 112 then operates the dispensing vertical position device 192 to lower the spray nozzle 204 toward the target position and into the selected well 50. After the spray nozzle 204 is lowered into the selected well 50, the LFDS controller 112 commands the metering pump 200 to dispense a specific amount of the selected experimental liquid formulation into the selected well 50 and thus, onto the plant specimen therein. The LFDS controller 112 then operates the dispensing vertical position device 192 to raise, or retract, the spray nozzle 204. The translation stage 116 is then operated to position a subsequent randomly selected well 50 at the target location directly under the spray nozzle 204. Whereupon, the spray nozzle 204 is lowered and the metering pump 200 dispenses a specific amount of the selected experimental liquid formulation into the subsequently randomly selected well 50.

This process is repeated until the LFDS controller 112 commands dispensing of a subsequent experimental liquid formulation. At which point, the dispensing vertical position device 192 raises the spray nozzle 204 to a home position and the dump drain 208 is moved to the deployed position under the spray nozzle 204. The metering pump 200 then flushes the feed tube 180 and the spray nozzle 204 with the subsequently selected experimental liquid formulation, as described above. When the flushing process is complete, the dump drain 208 is moved to the stowed position, and dispensing of the subsequently selected experimental liquid formulation is carried out in the same manner as the previous experimental liquid formulation, described above. The process of dispensing a selected experimental liquid formulation, flushing the feed tube 180 and the spray nozzle 204, and dispensing a subsequently selected experimental liquid formulation can be repeated until the plant specimens in each well 50 of each sample plate 46 has been sprayed with a selected liquid formulation.

Figure 11:
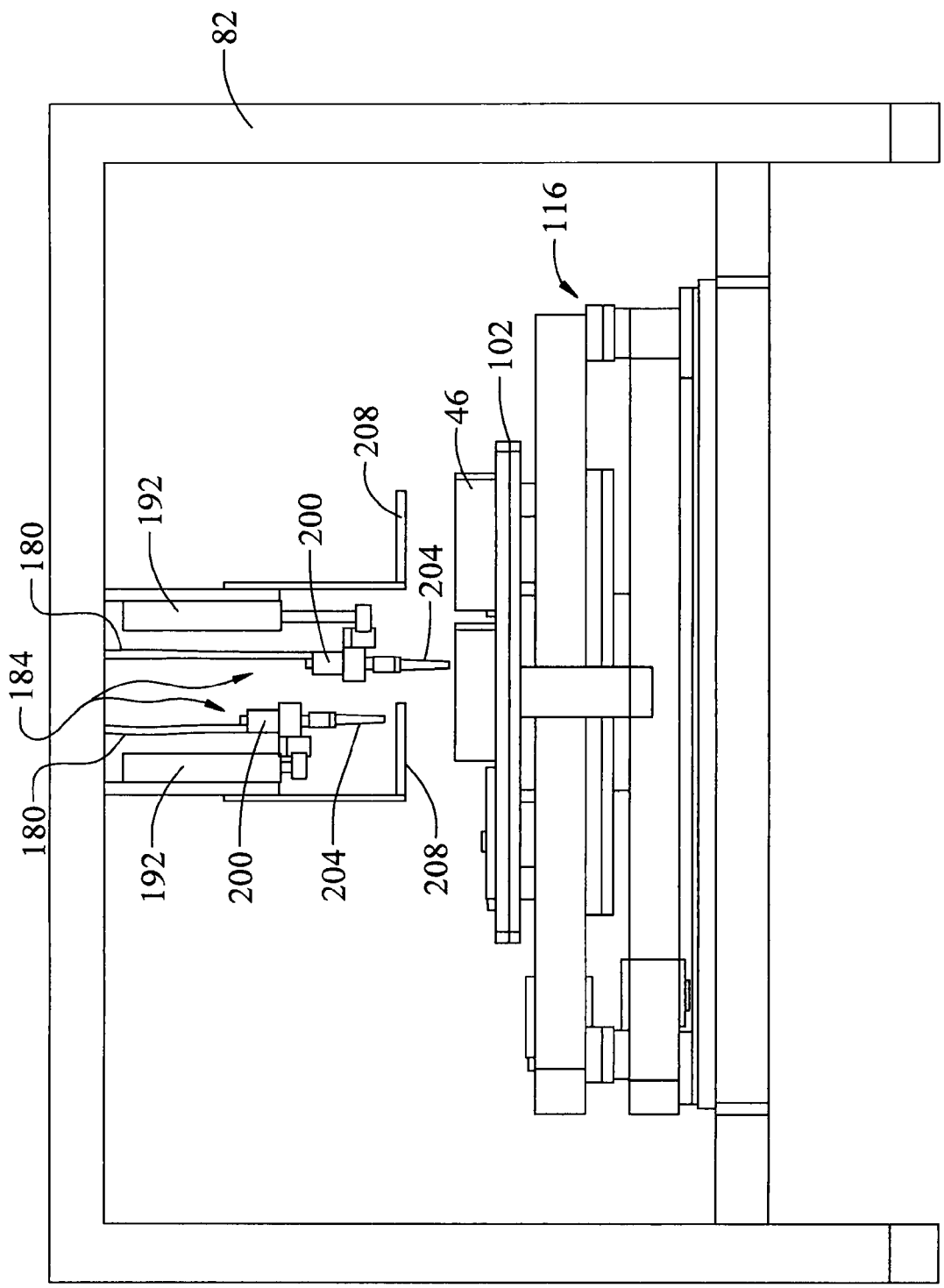
FIG. 11 is a rear view of the micro-sprayer assembly included in the LFDS shown in FIG. 4, in accordance with various other embodiments of the present disclosure.

Referring now to FIG. 11, in various embodiments the micro-sprayer assembly 94 includes two or more liquid formulation applicators 184. In such embodiments, the valve assembly 168 of the formulation withdrawal assembly 90 comprises a multi-port valve assembly, as described above. Additionally, each liquid formulation applicator 184 has the respective liquid formulation provided thereto by a separate feed line 180 connected to the multi-port valve assembly 168. Furthermore, each liquid formulation applicator 184 operates as described above and independently from each other. Thus, each liquid formulation applicator 184 can be operated independently to deliver precise quantities of different experimental liquid formulations to different sets of randomly selected sample wells 50.

Furthermore, as illustrated in FIG. 11, while a first liquid formulation applicator 184 is actively dispensing a selected liquid formulation to randomly selected sample wells 50, as described above, the LFDS controller 112 is flushing the feed tube 180 and spray nozzle 204 of a second inactive liquid formulation applicator 184, as described above. When the first liquid formulation applicator 184 has finished dispensing the selected liquid formulation, the dump drain 208 of the second, inactive liquid formulation applicator 184 is moved to the stowed position and the second liquid formulation applicator 184 becomes active and begins dispensing a subsequently liquid formulation. Substantially simultaneously, the first liquid formulation applicator 184 becomes inactive and its respective dump drain 208 is moved to the deployed position. Accordingly, the LFDS controller then initiates the flushing process of the feed tube 180 and spray nozzle 204 of the first (now inactive) liquid formulation applicator 184.

In various embodiments, the LFDS 22 is housed and operated within an environmentally controlled growth cabinet, or room, 214 simply illustrated as a block around the LFDS 22 in FIG. 4. The environment within the growth cabinet 214 is actively controlled to maintain a substantially consistent humidity and light intensity, e.g., 25% relative humidity and 400 ue to 500 ue, respectively. Additionally, the environment within the growth cabinet 214 is actively controlled to maintain a substantially consistent temperature during 'day time' hours, e.g., 24° C., and a substantially consistent temperature during 'night time' hours, e.g., 26° C. The controlled environment within the growth cabinet 214 provides a desired environment for the germination and growth of the plant specimens.

Figure 12:
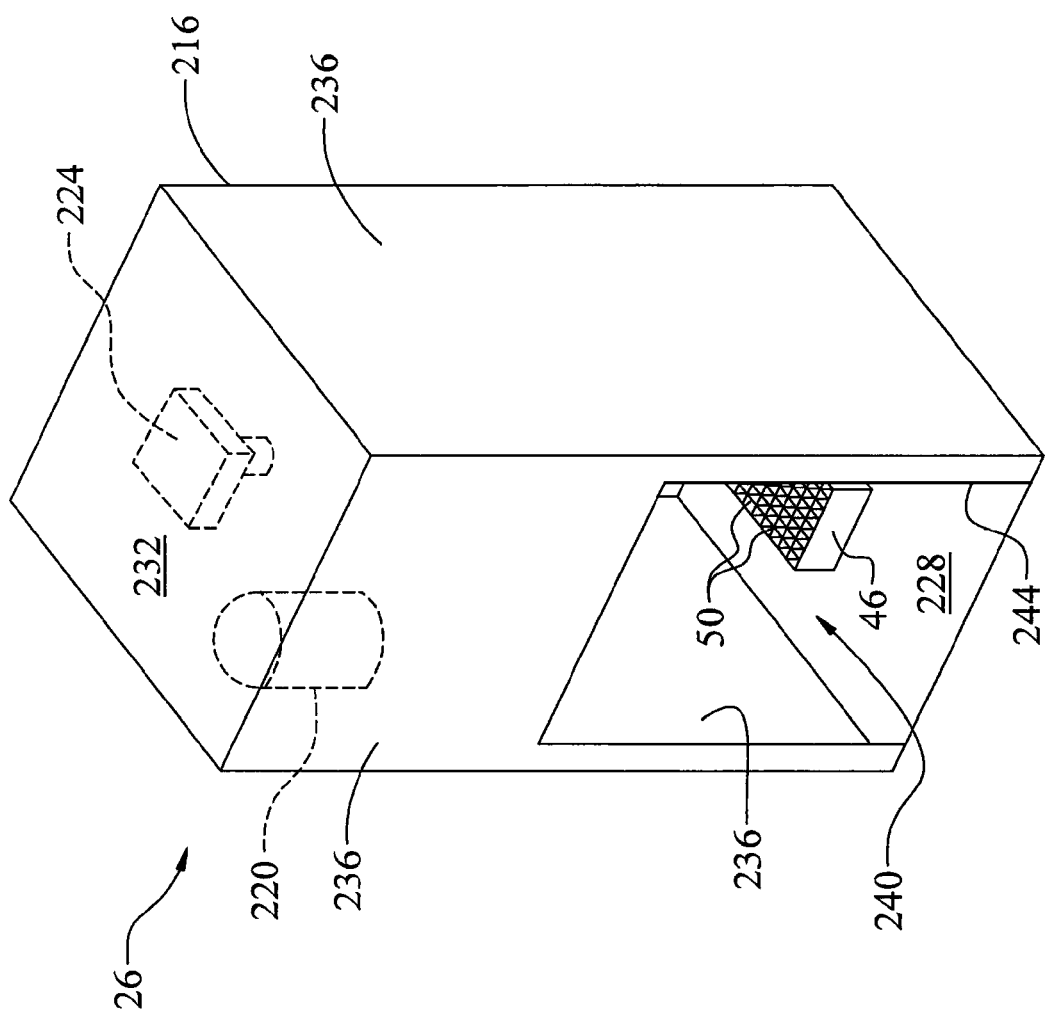
FIG. 12 is an isometric view of an imaging device included in the HTLFA system shown in FIG. 1, in accordance with various embodiments of the present disclosure.

FIG. 12 provides an exemplary illustration of the imaging system 26. Generally, the imaging system 26 includes a cabinet 216, a light source 220 and an imaging device 224. The cabinet 216 includes a bottom platform 228 sized to accommodate one or more of the sample plates 46 and top panel 232. The cabinet 216 additionally includes one or more walls 236 that enclose an imaging bay 240 with the exception of an opening 244 that allows for one or more sample plates 46 to be placed in and removed from the imaging bay 240, e.g., placed on and removed from the bottom platform 228. In various embodiments, the light source 220 and/or the imaging device 224 are attached to an inner surface of the top panel 232 and pointed downward toward the bottom platform 228. Alternatively, the light source 220 and/or the imaging device 224 can be attached to an inner surface of the wall(s) 236 and pointed downward toward the bottom platform 228.

The imaging device 26 can be any of a variety of imaging devices suitable for obtaining images of the seeded and sprayed sample plates 46 over a period of time, including without limitation, an optical camera, digital camera, time-lapse, video, or the like. In operation, one or more sample plates 46, for which one or more of the wells 50 have been sprayed with a selected experimental liquid formulation, is placed within the imaging bay 228, e.g., placed on the bottom platform 228. The light source 220 can be illuminated to provide proper lighting for imaging of the sample plate(s) 46. One or more images of the sample plate(s) 46 can be taken by the imaging device 224 at various intervals over a period of time to track and record changes in each of the plant specimens planted in each well 50. Particularly, the sequence of images can be used to analyze the plant specimens in each well 50 for the plant area and plant color over a designated period of time. Thus, the images of the specimens can be compared at selected intervals throughout the designated period of time to determine the efficacy of the individual experimental liquid formulations.

In various embodiments, the imaging device 224 is a digital camera and the digital images of the sample plates 46 are captured in controlled lighting conditions using a LemnaTec Scanalyzer (LemnaTec GmbH, Würselen, Germany) system at multiple time-points after application of the liquid formulation(s). The digital images captured by the LemnaTec Scanalyzer can then be analyzed and compared for the plant area and plant color of each well 50 over the selected period of time to determine the efficacy of the individual experimental liquid formulations.

Therefore, as discussed above, the HTLFA system 10 of the present disclosure allows for rapid and efficient analysis of various experimental liquid formulations to be applied to a plurality of plant specimens. In exemplary embodiments, the experimental liquid formulation can comprise herbicidal or fertilizer formulations such as herbicidal formulations comprising glyphosate. Particularly, in various embodiments, the high throughput systems, apparatus, and methods described above enable the precise and rapid analysis of the efficacy of experimental herbicidal and fertilizer formulations.

The present disclosure overcomes the difficulty of the current greenhouse method which is limited by greenhouse space and time. More specifically, the present disclosure provides a means to rapidly analyze experimental liquid formulations using a combinatorial approach with a minimum of space and labor inputs.

The above description of the disclosure is merely exemplary in nature and, thus, variations that do not depart from the gist of the disclosure are intended to be within the scope of the disclosure. Such variations are not to be regarded as a departure from the spirit and scope of the disclosure

EXAMPLE

This example describes the analysis of experimental glyphosate formulations using the HTLFA system 10 of the present disclosure.

The experiment comprised analyzing the effect of experimental glyphosate formulations on tobacco. Tobacco was chosen for use in the high-throughput assay because of its small seed size and small initial plant size. Also, tobacco is a broad leaf, which allows for better coverage of the spray application.

The experiment was begun by applying fine soil (Redi-Earth with 3 lb/yd$^3$ of 18-5-13 osmoform fertilizer) to each well of a 96-well polypropylene plate (2 ml, 96-well polypropylene from Whatman, Inc.). Each well of the plate was modified before use by inserting a drainage hole in the bottom of each well. A consistent amount of fine soil was added to each well using the soil jig 14, as described above.

A uniform amount of tobacco seed (Burley Tobacco from F.W. Rickard Seeds, Inc., Winchester, Ky.) was delivered to each well using the seed dispensing device 18, as described above.

The plates were sub-irrigated, overhead watered with a spray bottle if necessary, and placed in a growth cabinet under controlled growth conditions. Conditions in the cabinet were controlled using a 14-hour photoperiod, 24° C. night temperature, 26° C. day temperature, 25% relative humidity, and a light intensity of 400 ue to 500 ue. The plates were covered with lids for the first four days to allow the seed to germinate. After seven days in the growth cabinet, the plates were transferred to the moveable sample plate platform 102 of the LFDS 22, as described above and shown in FIGS. 4 through 11.

Various experimental glyphosate formulations were delivered to randomly selected wells of randomly selected plates using the LFDS 22. Once sprayed, the plates were returned to the growth cabinet and assessed for performance at multiple time points.

The performance of the various experimental glyphosate formulations was analyzed by capturing digital images that were evaluated using the LemnaTec Scanalyzer system, which analyses color and area of plants using image analysis software. Performance of the various experimental glyphosate formulations was then ranked based on leaf color and area with the more active chemistry being sent on for further testing within a standard greenhouse assay.

What is claimed is:

1. A high throughput system for analyzing the effect of a liquid formulation on a plant specimen, the system comprising:
    a liquid formulation dispensing subsystem (LFDS), the LFDS comprising:
    an automated moveable sample plate platform for holding at least one sample plate including a plurality of wells and for sequentially positioning select ones of the wells at a well target location, a plurality of the wells having a plant specimen therein;
    a micro-sprayer assembly including at least one applicator operable to apply discrete amounts of a liquid formulation to the plant specimens within each selected well when the selected wells are positioned at the well target location;
    an automated movable liquid formulation platform for holding at least one vial rack having placed therein a plurality of row of vials, the platform operable to position a selected row of vials at a vial target location, a plurality of vials each containing a different liquid formulation; and
    a formulation withdrawal assembly including a valve assembly having a plurality of uptake probes extending from a bottom edge, the formulation withdrawal assembly operable to:
        insert each of the uptake probes into a respective one of the vials in the row of vials positioned at the vial target location;
        withdraw at least a portion of a selected one of the liquid formulations from a respective vial; and
        provide the withdrawn liquid formulation to the micro-sprayer assembly.

2. The system of claim 1, wherein the at least one applicator comprises a formulation dispensing vertical position device operable to sequentially insert a spraying nozzle into each of the selected wells when the selected wells are positioned at the well target location.

3. The system of claim 2, wherein the spraying nozzle is an ultrasonic spraying nozzle.

4. The system of claim 2, wherein the applicator further comprises a metering pump in fluid communication with the spraying nozzle for metering the discrete amounts of liquid formulation applied to each plant specimen via the spraying nozzle.

5. The system of claim 1, wherein the automated movable liquid formulation platform is operable to sequentially position a plurality of selected rows of vials at the vial target location.

6. The system of claim 1, wherein the formulation withdrawal assembly further includes a formulation uptake vertical position device having the valve assembly connected thereto and operable to insert and withdraw the uptake probes into and out of the row of vials positioned at the vial target location.

7. The system of claim 1, wherein the LFDS further comprises a computer-based controller for controlling the operation of the automated moveable sample plate platform, the micro-sprayer assembly, the automated movable liquid formulation platform, and the formulation withdrawal assembly.

8. The system of claim 1, further comprising an environmentally controlled growth cabinet for housing the LFDS and the sample plates containing the plant specimens.

9. The system of claim 1, further comprising an imaging system for evaluating the efficacy of the formulation.

10. The system of claim 1, wherein the micro-sprayer assembly comprises a plurality of liquid formulation applicators operable such that while at least one of the plurality of liquid formulation applicators is applying discrete amounts of the liquid formulation to the plant specimens, at least one of the other liquid formulation applicators is undergoing a flushing process.

11. The system of claim 10, wherein each liquid formulation applicator comprises an automated dump drain operable to move between a stowed position for allowing the respective liquid formulation applicator to apply the liquid formulations formulation, and a deployed position for allowing the respective liquid formulation applicator to undergo the flushing process.

12. An automated method for assaying the efficacy of one or more liquid formulations on a plant specimen, the method comprising:
    moving a sample plate platform supporting at least one sample plate including a plurality of wells to sequentially position selected ones of the wells at a well target location, each selected well having a plant specimen therein;
    operating a micro-sprayer assembly to apply discrete amounts of at least one liquid formulation to the plant specimen within each selected well when the selected wells are positioned at the well target location;
    moving a liquid formulation platform supporting at least one vial rack having placed therein a plurality of rows of vials to sequentially position a plurality of selected rows of vials at a vial target location, a plurality of the vials containing a different one of a plurality of different liquid formulations; and
    operating a formulation withdrawal assembly, including a valve assembly having a plurality of uptake probes extending from a bottom edge, to:
        sequentially insert each of the uptake probes into a respective one of the vials in each selected row of vials as the selected rows are sequentially positioned at the vial target location;
        withdraw at least a portion of a selected one of the liquid formulations from a vial in each selected row as the rows are sequentially positioned at the vial target location; and provide the withdrawn liquid formulations to the micro-sprayer assembly.

13. The method of claim 12 further comprising: imaging the at least one sample plate after applying the at least one liquid formulation; and determining the efficacy of the at least one liquid formulation.

14. The method of claim 13, wherein determining the efficacy of the at least one liquid formulation comprises evaluating changes in the plant specimens using quantitative analysis of plant color and area.

15. The method of claim 12, wherein the method further comprises randomly selecting the wells to be sequentially positioned at the well target location.

16. The method of claim 12, wherein the method further comprises automatedly operating a formulation dispensing vertical position device to sequentially insert a spraying nozzle into each of the selected wells as the selected wells are sequentially positioned at the well target location.

17. The method of claim 16, wherein the spraying nozzle is an ultrasonic spraying nozzle.

18. The method of claim 12, wherein the micro-sprayer assembly comprises a plurality of liquid formulation applicators for applying the discrete amounts of the at least one liquid formulation to the plant specimens.

19. The method of claim 18, wherein the step of operating a micro-sprayer assembly comprises: operating at least one of the plurality of liquid formulation applicators to apply the discrete amounts of the at least one liquid formulation to the plant specimens; and substantially simultaneously performing a flushing process to at least one of the other liquid formulation applicators.

20. A liquid formulation dispensing system (LFDS) for applying one or more liquid formulations to a plurality of plant specimens, the system comprising:
   an automated moveable sample plate platform for holding at least one sample plate including a plurality of wells and for sequentially positioning selected ones of the wells at a well target location, each selected well having a plant specimen therein;
   a micro-sprayer assembly including at least one liquid formulation applicator operable to apply discrete amounts of a liquid formulation to the plant specimens within each selected well as the selected wells are sequentially positioned at the well target location;
   an automated movable liquid formulation platform for supporting at least one vial rack having placed therein a plurality of rows of vials and operable to sequentially position a plurality of selected rows of vials at a vial target location, a plurality of the vials each containing a different liquid formulations formulation; and
   a formulation withdrawal assembly including a valve assembly having a plurality of uptake probes extending from a bottom edge, the formulation withdrawal assembly operable to:
      insert each of the uptake probes into a respective one of the vials in the row of vials positioned at the vial target location;
      withdraw at least a portion of a selected one of the liquid formulations from the respective vial; and
      provide the withdrawn liquid formulation to the micro-sprayer assembly.

21. The system of claim 20, wherein the liquid formulation applicator comprises a formulation dispensing vertical position device operable to sequentially insert an ultrasonic spraying nozzle into each of the selected wells as the selected wells are sequentially positioned at the well target location.

22. The system of claim 20, wherein the liquid formulation applicator further comprises a metering pump in fluid communication with the spraying nozzle for metering the discrete amounts of liquid formulation applied to each plant specimen via the ultrasonic spraying nozzle as the ultrasonic spraying nozzle is sequentially inserted into each of the selected wells as the selected wells are sequentially positioned at the well target location.

23. The system of claim 20, wherein the formulation withdrawal assembly further includes a formulation uptake vertical position device having the valve assembly connected thereto and operable to insert and withdraw the uptake probes into and out of the row of vials sequentially positioned at the vial target location.

24. The system of claim 20, wherein the LFDS further comprises a computer-based controller for controlling the operation of the automated moveable sample plate platform, the micro-sprayer assembly, the automated movable liquid formulation platform, and the formulation withdrawal assembly.

25. The system of claim 20, wherein the micro-sprayer assembly comprises a plurality of liquid formulation applicators operable such that while at least one of the plurality of liquid formulation applicators is applying the discrete amounts of the liquid formulation to the plant specimens, at least one other liquid formulation applicator is undergoing a flushing process.

26. The system of claim 25, wherein each liquid formulation applicator comprises an automated dump drain operable to move between a stowed position for allowing the respective liquid formulation applicator to apply the liquid formulations formulation, and a deployed position for allowing the respective liquid formulation applicator to undergo the flushing process.

27. An automated, high throughput method for analyzing herbicidal formulations, the method comprising:
   moving a liquid formulation platform supporting at least one vial rack having placed therein a plurality of rows of vials to sequentially position a plurality of selected rows of vials at a vial target location, a plurality of the vials containing a different one of a plurality of different liquid formulations; and
   operating a formulation withdrawal assembly, including a valve assembly having a plurality of uptake probes extending from a bottom edge, to:
      sequentially insert each of the uptake probes into a respective one of the vials in each selected row of vials as the selected rows are sequentially positioned at the vial target location;
      withdraw at least a portion of a selected one of the liquid formulations from a vial in each selected row as the rows are sequentially positioned at the vial target location; and
      provide the withdrawn liquid formulations to a micro-sprayer assembly; moving a sample plate platform supporting at least one sample plate including a plurality of wells to sequentially position selected ones of the wells at a well target location, each selected well having a plant specimen therein; and
   operating the micro-sprayer assembly to apply discrete amounts of the selected liquid formulation to the plant specimen within each selected well as the selected wells are sequentially positioned at the well target location.

28. The method of claim 27 further comprising: imaging the plant specimens within each selected well after applying the discrete amounts of the selected liquid formulations; and determining the efficacy of the selected liquid formulations by quantitative digital analysis over time.

* * * * *

UNITED STATES PATENT AND TRADEMARK OFFICE
CERTIFICATE OF CORRECTION

| | |
|---|---|
| PATENT NO. | : 7,807,446 B2 |
| APPLICATION NO. | : 11/672210 |
| DATED | : October 5, 2010 |
| INVENTOR(S) | : Susan MacIsaac et al. |

It is certified that error appears in the above-identified patent and that said Letters Patent is hereby corrected as shown below:

Claim 11, Column 14, Lines 34-35: replace "formulations formulation" with -- formulation --

Claim 20, Column 15, Line 50: replace "formulations formulation" with -- formulation --

Claim 26, Column 16, Lines 29-30: replace "formulations formulation" with -- formulation --

Signed and Sealed this
Twenty-second Day of February, 2011

David J. Kappos
*Director of the United States Patent and Trademark Office*